United States Patent [19]
Peifer et al.

[11] Patent Number: 5,654,454
[45] Date of Patent: Aug. 5, 1997

[54] METALLOCENE PREPARATION AND USE

[75] Inventors: Bernd Peifer; Helmut G. Alt, both of Bayreuth, Germany; M. Bruce Welch, Bartlesville, Okla.

[73] Assignee: Phillips Petroleum Company, Bartlesville, Okla.

[21] Appl. No.: 452,946

[22] Filed: May 30, 1995

[51] Int. Cl.$^6$ .............................. C07F 17/00; C07F 7/28; C07F 9/00; C07F 11/00

[52] U.S. Cl. .................. 556/11; 556/43; 556/53; 556/58; 526/160; 526/943; 502/152; 502/158

[58] Field of Search ................. 556/53, 58, 43, 556/11; 526/160, 943

[56] References Cited

U.S. PATENT DOCUMENTS 4,147,709  4/1979  Lynch .................... 260/429.3

OTHER PUBLICATIONS

Parkin et al. Organometallics, vol. 8, No. 5, pp. 1172–1179 (1989).

J. Organometallic Chemistry, 456, pp. 89–95 (1993).

*Primary Examiner*—Porfirio Nazarid-Gonzalez
*Attorney, Agent, or Firm*—Edward L. Bowman

[57] ABSTRACT

Double bound metallocenes, i.e. metallocenes having a cyclopentadienyl-containing radical that is bound to a transition metal both by a pi bond and by a sigma carbon bond of a substituent of that same cyclopentadienyl-containing radical can be prepared by reducing metallocenes having a cyclopentadienyl-containing radical having at least one an unsaturated substituent. Also a process for producing polymers comprising contacting at least one olefinic monomer under suitable polymerization conditions with such double bound metallocenes.

11 Claims, No Drawings

METALLOCENE PREPARATION AND USE

FIELD OF THE INVENTION

This invention relates to metallocenes. In a more specific aspect this invention relates to metallocenes containing at least one cyclopentadienyl radical which is bonded to a transition metal of the metallocene by both pi bonding and by a carbon sigma bond of a substituent of said cyclopentadienyl radical. In still another aspect this invention relates to the use of metallocenes in the polymerization of olefinically unsaturated monomers.

BACKGROUND OF THE INVENTION

The term "Metallocene" as used herein refers to a derivative of cyclopentadienylidene which is a metal derivative containing at least one cyclopentadienyl component which is bonded to a transition metal. The transition metal is selected from Groups IVB, VB, and VIB, preferably IVB and VIB. Examples include titanium, zirconium, hafnium, chromium, vanadium, as well as rare earth metals. A number of metallocenes have been found to be useful for the polymerization of olefins. Generally, the more preferred catalysts are metallocenes of Zr, Hf, or Ti. The term "sandwich-bonded metallocene" is used herein to refer to metallocenes having at least two cyclopentadienyl groups that are both pi bonded to the same transition metal atom.

Numerous types of metallocenes are known in the art. The metallocenes of the present invention differ from most in that at least one of the cyclopentadienyl-containing radicals that is pi bonded to the transition metal has a substituent that is also bonded to a transition metal but through a carbon sigma bond to the metal. Such metallocenes are referred to herein as double bound metallocenes. Only one example of such a double bound metallocene is believed to have ever been heretofore disclosed. It is (cyclopentadienyl) ((cyclopentadienyl)(dimethyl)methane (1-indanyl)) zirconium (IV) chloride, the preparation of which is disclosed in *J. Organomet. Chem.*, 456, 89–95(1993), an article coauthored by one of the present coinventors, see the compound of formula (4) on page 90 of that article.

Accordingly, one object of the present invention is to provide a new class of metallocenes.

Another object of the present invention is to provide methods for producing such metallocenes.

Another object of the present invention is provide a method for producing polymers by polymerizing olefins using double bound metallocenes.

Other aspects, objects, and advantages of the present invention will be apparent from the following disclosure.

SUMMARY OF THE INVENTION

In accordance with the present invention there is provided a process for forming a metallocene having a cyclopentadienyl-containing radical that is bound to a transition metal both by a pi bond and by a carbon sigma bond of a substituent of that same cyclopentadienyl-containing radical comprising subjecting a specific type of metallocene to reaction with a reducing agent, said specific type of metallocene being one selected from the group consisting of metallocenes having a cyclopentadienyl-containing radical having at least one unsaturated substituent, preferably an olefinically unsaturated substituent, other than metallocenes having as their organic ligands (cyclopentadienyl) ((cyclopentadienyl) (1-indanyl)(dimethyl) methane). In accordance with still another object of the present invention there is provided a process for producing polymers comprising contacting at least one olefinic monomer under suitable polymerization conditions with a double bound metallocene.

DETAILED DESCRIPTION OF THE INVENTION

The term double bound metallocene includes metallocenes having a cyclopentadienyl-containing radical that is either (1) bound to the same transition metal both by a pi bond and by a sigma bond of a substituent of that cyclopentadienyl-containing radical or (2) bound to one transition metal of one molecule of the precursor metallocene by a pi bond and to the transition metal of another molecule of the precursor metallocene by a carbon sigma bond of a substituent of that cyclopentadienyl radical. Examples of the first type of double bound metallocene include those of the formula

 (I)

wherein each Z is the same or different cyclopentadienyl-containing radical, R is a divalent organo radical connecting the two Z radicals, x is 1 or 0, R' is a divalent organo radical which connects Z and Me in such a fashion that there are only four atoms separating the connected Z and Me and those atoms are carbon atoms, Me is a transition metal, and Q is selected from the group consisting of hydrocarbyl, hydrocarbyloxy, and halides Examples of the second type of double bound metallocene include those metallocenes having at least one unit of the formula

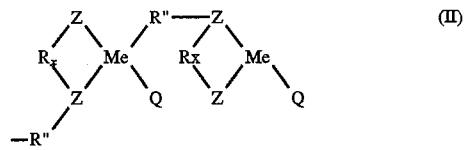 (II)

wherein Z, Me, Q, and x are as defined above and wherein R is a divalent organo radical connecting a Z to an Me, said R" being such that the number of atoms separating the respective joined Z and Me is either 2 or 3 or more than 4.

Typically if Q is hydrocarbyl it will contain 1 to 20 carbon atoms, more preferably 1 to 4 carbon atoms. R' can be selected from wide range of organo radicals. It is currently preferred for R' to be hydrocarbyl. R can likewise be selected from a wide range of organo radicals, typically it will contain 1 to 20 carbon atoms. R can be selected from any of the divalent organo radicals known in the art as suitable for forming a bridge between two cyclopentadienyl-radicals. Examples include saturated divalent hydrocarbyl radicals, such as, for example alkylene radicals having 1 to 20 carbon atoms, divalent organo silylene radicals, such as, for example dihydrocarbyl divalent silylene radicals such as dimethyl silane, diphenyl silane, and methyl diphenyl silane, and divalent dihydrocarbyl tin radicals, such as for example, dimethyl tin and diphenyl tin. Generally R will have 1 to 20 carbon atoms. In a currently preferred embodiment R is selected from divalent organo radicals such that there is only one atom in R which separates the two Z radicals. R" can be selected from a wide range of organic radicals. It is currently preferred for Me to be selected from Zr, Hf, and Ti.

The term cyclopentadienyl-radical as used herein refers to radicals having cyclopentadienyl structure, examples include substituted or unsubstituted forms of cyclopentadienyl, indenyl, tetrahydroindenyl, fluorenyl, octahydrofluorenyl, benzofluorenyl, and the like. The substituents of such cyclopentadienyl-containing radicals can, if present, can take essentially any form that does not interfere with the desired reactions. Typically the substituents, if present, are organo radicals, more typically hydrocarbyl or hydrocarbyloxy radicals, generally containing 1 to 20 carbon atoms. It is currently preferred for the special metallocene initial reactant to have two halide transition metal bonds.

The reduction step involved in preparing the double bound metallocenes can be carried out using a variety of known reducing treatments. Typically the metallocene, preferably a metallocene having a halide bonded to the transition metal, is contacted with a reducing agent in a suitable liquid diluent. In general, the conditions employed are the same type of conditions that have in the past been found suitable for the production of the Schwartz reagent and similar compounds. Some examples of such techniques are disclosed in U.S. Pat. No. 4,147,709. For example, the special type of metallocene initial reactant in which one of the cyclopentadienyl-containing radicals has a substituent having unsaturation can be contacted with a reducing agent such as LiAlH$_4$ or LiAlH-(O-t-butyl)$_3$. The ratio of the reducing agent to the metallocene can vary over a wide range but typically would be employed in the amount or about 1 mole per mole of metallocene reactant. Any suitable liquid diluent could be employed. The term "liquid diluent" as used herein includes hydrocarbons such as isobutane, pentane, benzene, toluene, and the like as well as ethers such as diethylether and tetrahydrofuran, and haloorganic liquids, such as dichloromethane.

Another example would involve treating the special metallocene with a solution of NaAlH$_2$(OCH$_2$CH$_2$OCH$_3$)$_2$ and benzene. Still another technique would involve treating the starting metallocene with metallic magnesium in tetrahydrofuran. Still another technique would involve reacting the metallocene with molecular hydrogen in the presence of an elemental metal selected from Group IA of the Periodic Table in a solvent for the metallocene that does not prevent formation of the desired product.

The reaction conditions can vary over a wide range depending upon the particular results desired. Obviously it is desirable to limit the temperature to a temperature below that which would decompose the desired product.

The double bound metallocenes have been found to be useful as components for polymerization catalyst systems. The inventive catalyst systems are particularly useful for the polymerization of alpha-olefins having 2 to 10 carbon atoms. Examples of such olefins include ethylene, propylene, butene-1, pentene-1, 3-methylbutene-1, hexene-1, 4-methylpentene-1, 3-methylpentene-1, heptene-1, octene-1, decene-1, 4,4-dimethyl-1-pentene, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin. Styrene and butadiene are also examples of olefinically unsaturated monomers.

The polymerizations can be carried out under a wide range of conditions depending upon the particular metallocene employed and the particular results desired. The inventive catalyst system is considered useful for polymerization conducted under solution, slurry, or gas phase reaction conditions.

When the polymerizations are carried out in the presence of liquid diluents obviously it is important to use diluents which do not have an adverse effect upon the catalyst system. Typical liquid diluents include propylene, propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

Typically the inventive metallocene would be used with a suitable cocatalyst. Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of trimethylaluminum and dimethylfluoroaluminum such as disclosed by Zambelli et, *Macromolecules*, 22, 2186 (1989). In such counter anion systems the cocatalyst can be viewed as an ion-exchange compound comprising a cation which will irreversibly react with as least one ligand contained in the metallocene and a non-coordination anion which is either a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

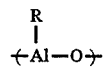

where R is generally a hydrocarbyl group having 1 to 5 carbon atoms.

Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane. Aluminoxanes, also sometimes referred to as poly (hydrocarbyl aluminum oxides) are well known in the art and are generally prepared by reacting an hydrocarbylaluminum compound with water. Such a preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the double bound metallocene can be employed in combination with a solid organoaluminoxane which is substantially insoluble in the polymerization diluent under particle form polymerization conditions. The organo aluminoxane component used in preparing the inventive solid catalyst system include oligomeric aluminum compounds having repeating units of the formula

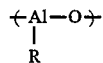

Some examples are often represented by the general formula (R—Al—O)$_n$ or R(R—Al—O—)$_n$AlR$^2$. In the general alumoxane formula R is preferably a $C_1$-$C_5$ alkyl radical, for example, methyl, ethyl, propyl, butyl or pentyl and "n" is an integer from 1 to about 50. Most preferably, R is methyl and "n" is at least 4. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique of producing a solid cocatalyst involves contacting an organoaluminoxane with an organic borane compound free of acidic hydrogen as taught U.S. Pat. No. 5,354,721, the disclosure of which is incorporated herein by reference. Yet another technique involves contacting an organoaluminoxane with an organoboron compound having boron acid functionality, i.e. —BOH, as taught in U.S. Pat. No. 5,414,189, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. Pat. No. 5,411,925, the disclosure of which is incorporated herein by reference.

In a particularly preferred embodiment of the present invention the double bound metallocene is subjected to prepolymerization with an olefin to produce a solid catalyst system that can later be used in the polymerization of olefins. This technique is particularly useful in slurry or particle-form type polymerizations.

To prepare the solid prepolymerized catalyst system the metallocene and aluminoxane are combined in the presence of a suitable liquid to form a liquid catalyst system. It is preferred that the liquid catalyst system be prepared using an organic liquid in which the aluminoxane is at least partially soluble. The currently preferred liquids are hydrocarbons such as hexane or toluene. Typically an aromatic liquid solvent is employed. Examples include benzene, toluene, ethylbenzene, diethylbenzene, and the like. The amount of liquid to be employed is not particularly critical. Nevertheless, the amount should preferably be such as to dissolve at least a portion of the product of the reaction between the metallocene and the aluminoxane, provide desirable polymerization viscosity for the prepolymerization, and to permit good mixing. The temperature is preferably kept below that which would cause the metallocene to decompose. Typically the temperature would be in the range of −50° C. to 100° C. Preferably, the metallocene, the aluminoxane, and the liquid diluent are combined at room temperature, i.e. around 10° to 30° C. The reaction between the aluminoxane and the metallocene is relatively rapid. The reaction rate can vary depending upon the ligands of the metallocene. It is generally desired that they be contacted for at least about a minute to about 1 hour.

It is within the scope of the invention to form the liquid catalyst system in the presence of a particulate solid. Any number of particulate solids can be employed as the particulate solid. Typically the support can be any organic or inorganic solid that does not interfere with the desired end result. Examples include porous supports such as talc, inorganic oxides, and resinous support materials such as particulate polyolefins. Examples of inorganic oxide materials include Groups II, III, IV or V metal oxides such as silica, alumina, silica-alumina, and mixtures thereof. Other examples of inorganic oxides are magnesia, titania, zirconia, and the like. Other suitable support materials which can be employed include materials such as, magnesium dichloride, and finely divided polyolefins, such as polyethylene. It is within the scope of the present invention to use a mixture of one or more of the particulate solids.

It is generally desirable for the solid to be thoroughly dehydrated prior to use, preferably it is dehydrated so as to contain less than 1% loss on ignition. Thermal dehydration treatment may be carried out in vacuum or while purging with a dry inert gas such as nitrogen at a temperature of about 20° C. to about 1000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the solid to a chemical treatment in order to remove water and reduce the concentration of surface hydroxyl groups. Chemical treatment is generally capable of converting all water and hydroxyl groups in the oxide surface to relatively inert species. Useful chemical agents are for example, trimethylaluminum, ethyl magnesium chloride, chlorosilanes such as $SiCl_4$, disilazane, trimethylchlorosilane, dimethylaminotrimethylsilane and the like.

The chemical dehydration can be accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichlorodimethylsilane. The solution is added slowly to the slurry. The temperature ranges during chemical dehydration reaction can be from about 0 ° C. to about 120° C., however, higher and lower temperatures can be employed. Preferably, the temperature will be about 15 ° C. to about 100 ° C. The chemical dehydration procedure should be allowed to proceed until all the substantially reactive groups are removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material may be filtered under a nitrogen atmosphere and washed one or more times with a dry, oxygen free inert solvent. The wash solvents as well as the diluents employed to form the slurry and the solution of chemical dehydrating agent, can be any suitable inert hydrocarbon. Illustrative of such hydrocarbons are pentane, heptane, hexane, toluene, isopentane and the like.

Another chemical treatment that can be used on solid inorganic oxides such as silica involves reduction by contacting the solid with carbon monoxide at an elevated temperature sufficient to convert substantially all the water and hydroxyl groups to relatively inactive species.

The specific particle size of the support or inorganic oxide, surface area, pore volume, and number of hydroxyl groups is not considered critical to its utility in the practice of this invention. However, such characteristics often determine the amount of support to be employed in preparing the catalyst compositions, as well as affecting the particle morphology of polymers formed. The characteristics of the carrier or support must therefore be taken into consideration in choosing the same for use in the particular invention.

It is also within the scope of the present invention to add such a particulate solid to the liquid catalyst system after it has been formed and to carry out the prepolymerization in the presence of that solid.

The amount of aluminoxane and metallocene used in forming the liquid catalyst system for the prepolymerization can vary over a wide range. Typically, however, the molar ratio of aluminum in the aluminoxane to transition metal of the metallocene is in the range of about 1:1 to about 20,000:1, more preferably, a molar ratio of about 50:1 to about 2000:1 is used. If a particulate solid, i.e. silica, is used generally it is used in an amount such that the weight ratio of the metallocene to the particulate solid is in the range of about 0.00001/1 to 1/1, more preferably 0.0005/1 to 0.2/1.

The prepolymerization is conducted in the liquid catalyst system, which can be a solution, a slurry, or a gel in a liquid. A wide range of olefins can be used for the prepolymerization. Typically, the prepolymerization will be conducted using an olefin, preferably selected from ethylene and non-aromatic alpha-olefins, and as propylene. It is within the scope of the invention to use a mixture of olefins, for example, ethylene and a higher alpha olefin can be used for the prepolymerization.

The prepolymerization can be conducted under relatively mild conditions. Typically, this would involve using low pressures of the olefin and relatively low temperatures designed to prevent site decomposition resulting from high concentrations of localized heat. The prepolymerization typically occurs at temperatures in the range of about $-30°$ C. to about $+110°$ C., more preferably in the range of about $+10°$ to about $+30°$ C. The amount of prepolymer can be varied but typically would be in the range of from about 1 to about 95 wt % of the resulting prepolymerized solid catalyst system, more preferably about 5 to 80 wt %. It is generally desirable to carry out the prepolymerization to at least a point where substantially all of the metallocene is in the solid rather than in the liquid since that maximizes the use of the metallocene.

After the prepolymerization, the resulting solid prepolymerized catalyst is separated from the liquid of the reaction mixture. Various techniques known in the art can be used for carrying out this step. For example, the material could be separated by filtration, decantation, or by vacuum evaporation. It is currently preferred, however, not to rely upon vacuum evaporation since it is considered desirable to remove substantially all of the soluble components in the liquid reaction product of the prepolymerization from the resulting solid prepolymerized catalyst before it is stored or used for subsequent polymerization. After separating the solid from the liquid, the resulting solid is preferably washed with a hydrocarbon and then dried using high vacuum to remove substantially all the liquids and other volatile components that might still be associated with the solid. The vacuum drying is preferably carried out under relatively mild conditions, i.e. temperatures below 100° C. More typically the prepolymerized solid is dried by subjection to a high vacuum at a temperature of about 30 ° C. until a substantially constant weight is achieved. A preferred technique employs at least one initial wash with an aromatic hydrocarbon, such as toluene, followed by a wash with a paraffinic hydrocarbon, such as hexane, and then vacuum drying.

It is within the scope of the present invention to contact the prepolymerization reaction mixture product with a liquid in which the prepolymer is sparingly soluble, i.e. a counter solvent for the prepolymer, to help cause soluble prepolymer to precipitate from the solution. Such a liquid is also useful for the subsequent washing of the prepolymerized solid.

It is also within the scope of the present invention to add a particulate solid of the type aforementioned after the prepolymerization. Thus one can add the solid to the liquid prepolymerization product before the counter solvent is added. In this manner soluble prepolymer tends to precipitate onto the surface of the solid to aid in the recovery of the filtrate in a particulate form and to prevent agglomeration during drying. The liquid mixture resulting from the prepolymerization or the inventive solid prepolymerized catalyst can be subjected to sonification to help break up particles if desired.

Further, if desired the recovered solid prepolymerized catalyst system can be screened to give particles having sizes that meet the particular needs for a particular type of polymerization.

Another option is to combine the recovered inventive solid prepolymerized catalyst system with an inert hydrocarbon, such as one of the type used as a wash liquid, and then to remove that liquid using a vacuum. In such a process it is sometimes desirable to subject the resulting mixture to sonification before stripping off the liquid.

The resulting solid prepolymerized metallocene-containing catalyst system is useful for the polymerization of olefins. Generally, it is not necessary to add any additional aluminoxane to this catalyst system. In some cases it may be found desirable to employ small amounts of an organoaluminum compound as a scavenger for poisons. The term organoaluminum compounds include compounds such as triethylaluminum, trimethylaluminum, diethylaluminum chloride, ethylaluminum dichloride, ethylaluminum sesquichloride, and the like. Trialkylaluminum compounds are currently preferred. Also in some applications it may be desirable to employ small amounts of antistatic agents which assist in preventing the agglomeration of polymer particles during polymerization. Still further, when the inventive catalyst system is added to a reactor as a slurry in a liquid, it is sometimes desirable to add a particulate dried solid as a flow aid for the slurry. Preferably the solid has been dried using one of the methods described earlier. Inorganic oxides such as silica are particularly preferred. Currently, it is preferred to use a fumed silica such as that sold under the trade name Cab-o-sil. Generally the fumed silica is dried using heat and trimethylaluminum.

The solid prepolymerized catalyst system is suitable for use in the polymerization of olefinically unsaturated monomers. Such polymerizations can be carried out under gas phase, solution phase, or slurry phase conditions. The conditions used would be generally the same as those used when other solid metallocenes are used in such polymerizations. One difference is that generally it is not necessary to employ an additional cocatalyst with the solid prepolymerized catalyst.

9

The polymers produced with the catalysts herein disclosed have a wide range of uses that will be apparent to those skilled in the art from the physical properties of the respective polymers. Applications such as molding, films, adhesives, and the like are indicated.

A further understanding of the present invention, its various aspects, objects and advantages will be provided by the following examples.

EXAMPLE I

The unbridged metallocene (cyclopentadienyl) (omega butenylcyclopentadienyl) zirconium dichloride which could also be named (cyclopentadienyl) (1-but-3-enyl-cyclopentadienyl) zirconium dichloride in the amount of 3 mmoles was dissolved in tetrahydrofuran along with 0.79 g (3.11 mmoles) of lithium aluminum tri-tert butyloxy hydride and stirred overnight at room temperature. The liquid was then evaporated in a vacuum and the residue was extracted with chloroform over sodium sulfate. The resulting liquid was concentrated by evaporation and then crystallized by the addition of n-hexane. The double bound unbridged metallocene product (cyclopentadienyl) (1-butanyl cyclopentadienyl) zirconium (IV) chloride was identified by both hydrogen and carbon $^{13}$NMR as having the butanyl bound to the zirconium by a sigma bond and the two cyclopentadienyl groups bound to the zirconium by pi bonds.

Similar reactions were carried out by starting with the following different metallocenes, namely the bridged sandwich bonded metallocenes ((but-3-enyl cyclopentadienyl) (fluorenyl) (dimethyl) methane) zirconium dichloride, ((omegabutenylindenyl) (fluorenyl) (dimethyl) silane) zirconium dichloride, and ((fluorenyl) (ethene cyclopentadienyl)(dimethyl)methane) zirconium dichloride. The recovered products were also identified by hydrogen and carbon $^{13}$NMR as double bound metallocenes.

The resulting products can be referred to respectively as ((fluorenyl) (butanyl cyclopentadienyl) (dimethyl) methane) zirconium (IV) chloride ((fluorenyl) (butanyl indenyl) (dimethyl) silane) zirconium (IV) chloride and poly( (fluorenyl) (ethanyl cyclopentadienyl) (dimethyl) methane) zirconium (IV) chloride, an example of a double bound metallocene of formula (II)

EXAMPLE II

The butanyl-containing double bound metallocenes prepared as described in Example I, i.e. metallocenes of formula (I), were evaluated for their effectiveness in the polymerization of ethylene. In addition, a comparable polymerization was carried out using the double bound metallocene (cyclopentadienyl)((cyclopentadienyl) (dimethyl) methane (1-indanyl)) zirconium (IV) chloride, i.e. the compound of formula (4) of the aforementioned article in the J. Organomet. Chem. The polymerizations involved preparing a catalyst solution by adding about 1 to 2 mg of the metallocene to a Schlenk tube and mixing it with 1 mL of a 30 weight percent toluene solution of methylaluminoxane. The solution was then diluted with toluene so that about 0.2 to about 0.5 mg of the metallocene complex was dissolved in about 10 mL. Ethylene was polymerized at room temperature in the Schlenk tube using slight excess pressure. The color was monitored. In each case, the color of the liquid portion was diminished indicating that the complex became immobilized in the formed polymer, i.e. there was evidence that the metallocene was incorporated in the polymer.

EXAMPLE III

Using four different double bound metallocenes four different solid catalyst systems were prepared.

First, the poly ((ethanyl-cyclopentadienyl) (fluorenyl) (dimethyl) methane) zirconium (IV) chloride, that was prepared in Example I, in the amount of about 0.1 g was combined with a trimethylaluminum treated Davidson 948 silica. In a dry box this solid was combined with 20 mL of a 1.1 molar toluene solution of methylaluminoxane obtained from Schering. The resulting mixture was stirred for 1 hour and then washed and filtered two times with 25 mL of hexane. The color of the wash had just a trace of the color of the metallocene. The recovered solid was placed under a high vacuum for 2 hours and recovered as solid catalyst system A.

In another case, 0.27 g of the double bond metallocene ((butanylcyclopentadienyl) (fluorenyl) (dimethyl)methane) zirconium (IV) chloride was mixed with 25.1 mL of a 1.1. molar toluene solution of methylaluminoxane obtained from Schering. To this mixture was added 2.5 g of a trimethylaluminum (TMA) treated Davidson 948 silica. The resulting mixture was stirred for 20 minutes. Then while at room temperature the mixture was contacted with 5 psig of ethylene for 1 hour. The color changed from reddish orange to purple about 5 minutes after starting the ethylene. The resulting solid was washed and filtered two times with 20 mL of toluene and two times with 20 mL of hexane. Then the recovered solid was exposed to 2 hours of high vacuum to yield solid prepolymerized catalyst system B.

In yet another run, 0.256 of the double bound metallocene ((fluorenyl) (butanyl-indenyl) (dimethyl) silane) zirconium chloride was combined with 23 mL of a 1.1 molar toluene solution of methylaluminoxane obtained from Schering. To this was added 2.5 g of the TMA treated Davidson 948 silica. The resulting mixture was stirred for 20 minutes then was exposed to 5 psig of ethylene to effect prepolymerization. The color changed from reddish brown to dark purple within 10 minutes after the beginning of ethylene addition. After 1 hour, the solid was recovered and washed and filtered two times with 20 mL of toluene and two times with 20 mL of hexane. The resulting solid was then subjected to a high vacuum for 2 hours to result in solid prepolymerized catalyst system C.

Still another solid catalyst was prepared by mixing 0.265 g of the double bound metallocene (cyclopentadienyl) ((cyclopentadienyl) (dimethyl) methane (indanyl) zirconium (IV) chloride with 27.4 mL of a 1.1 molar toluene solution of methylaluminoxane obtained from Schering. To this was added 2.5 g of TMA treated Davidson 948 silica and the mixture was stirred for 2 hours. Then ethylene was introduced at 5 psig and room temperature. After 1 hour the resulting solid was washed and filtered two times each with 20 mL of toluene and 20 mL of hexane. The resulting solid was then subjected to a high vacuum for 2 hours to yield solid prepolymerized catalyst system D.

EXAMPLE IV

Each of the catalysts A–D were individually employed in polymerization reactions. These polymerizations were conducted in a one-gallon stirred autoclave reactor. The catalyst system was charged to the autoclave. The autoclave was filled with 2 liters of isobutane and the temperature raised to about 90° C. Hydrogen was added from a 300 cc vessel and then the vessel was pressurized to a total reactor pressure of 450 psig with ethylene. All the polymerizations except 1 were continued for 1 hour. The reactor was then cooled and vented and the solid polymer was recovered. The results are summarized in Table I.

TABLE I

| Run No. | Catalyst | H₂ psi | Density | M_w × 100 | HI | MI | SR |
|---|---|---|---|---|---|---|---|
| 1 | A | 33.6 | 0.9484 | 116 | 2.6 | 0.42 | 18 |
| 2 | A | 13.3 | 0.9482 | 101 | 2.3 | 0.62 | 20 |
| 3 | B* | 10 | — | — | — | 1.83 | 18 |
| 4 | B | 10 | — | — | — | 1.36 | 20 |
| 5 | B | 10 | 0.9488 | 80 | 2.3 | 1.99 | 16 |
| 6 | C | 10 | 0.9581 | 99 | 5.2 | 0.67 | 44 |
| 7 | D | 10 | — | — | — | 1800 | — |
| 7 | D | 10 | 0.9784 | 16.8 | 2.9 | — | — |

*Only 30 minutes of polymerization

The solid catalyst systems A, B, and D gave polymers having a narrow molecular weight distribution of the type generally associated with "single site" metallocene catalysts, i.e. HI's of less than 3. Solid catalyst C gave a slightly broader molecular weight distribution.

That which is claimed is:

1. A process for producing a metallocene having a cyclopentadienyl-containing radical that is bound to a transition metal selected from the group consisting of metals of Groups IVB, VB, and VIB of the Periodic Table including the rare earth metals both by a pi bond and by a carbon sigma bond of a substituent of that same cyclopentadienyl-containing radical comprising subjecting a specific type of metallocene to reaction with a reducing agent, said specific type of metallocene being one selected from the group consisting of metallocenes having a cyclopentadienyl-containing radical having at least one unsaturated substituent, other than the metallocenes having as their organic ligands (cyclopentadienyl) ((cyclopentadienyl) (indenyl)(dimethyl) methane).

2. A process according to claim 1, which produces a double bound metallocene selected from those of the formula

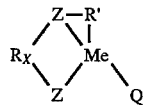

wherein each Z is the same or different cyclopentadienyl-containing radical, R is a divalent organo radical connecting the two Z radicals, x is 1 or 0, R' is a divalent organo radical which connects Z and Me in such a fashion that there are only four atoms separating the connected Z and Me and those atoms are carbon atoms, Me is a transition metal selected from the group consisting of metals of Groups IVB, VB, and VIB of the Periodic Table including the rare earth metals, and Q is selected from the group consisting of hydrocarbyl, hydrocarbyloxy, and halides and metallocenes having at least one unit of the formula

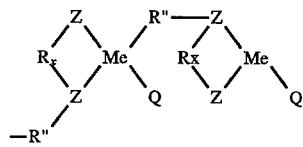

wherein Z, Me, Q, and x are as defined above and wherein R" is a divalent organo radical connecting a Z to an Me, said R" being such that the number of atoms separating the respective joined Z and Me is either 2, 3 or more than 4, with the proviso that the metallocenes of formula (I) not include sandwich-bonded metallocenes having as their organic ligands the combination of (cyclopentadienyl) and ((cyclopentadienyl) (indanyl) (dimethyl) methane).

3. A process according to claim 1 which produces the metallocene (cyclopentadienyl) (butanyl cyclopentadienyl) zirconium (IV) chloride.

4. A process according to claim 1 which produces the metallocene ((fluorenyl) (butanyl cyclopentadienyl) (dimethyl) methane) zirconium (IV) chloride.

5. A process according to claim 1 which produces the metallocene ((fluorenyl) (butanyl indenyl) dimethyl silane) zirconium (IV) chloride.

6. A process according to claim 1 which produces a metallocene of formula (II) wherein the Z attached to R" is cyclopentadienyl, the other Z is fluorenyl, R is dimethymethylene, R" is the saturated divalent ethylene radical, Me is Zr, and Q is Cl.

7. A double bound metallocene selected from those of the formula

wherein each Z is the same or different cyclopentadienyl-containing radical, R is a divalent organo radical connecting the two Z radicals, x is 1 or 0, R' is a divalent organo radical which connects Z and Me in such a fashion that there are only four atoms separating the connected Z and Me and those atoms are carbon atoms, Me is a transition metal selected from the group consisting of metals of Groups IVB, VB, and VIB of the Periodic Table including the rare earth metals, and Q is selected from the group consisting of hydrocarbyl, hydrocarbyloxy, and halides and metallocenes have at least one unit of the formula

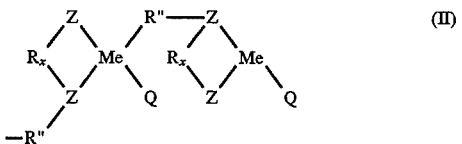

wherein Z, Me, Q, and x are as defined above and wherein R" is a divalent organo radical connecting a Z to an Me, said R" being such that the number of atoms separating the respective joined Z and Me is 2, 3 or more than 4, with the proviso that the metallocenes of formula (I) not include sandwich-bonded metallocenes having as their organic ligands the combination of (cyclopentadienyl) and ((cyclopentadienyl) (indanyl)(dimethyl) methane).

8. A metallocene according to claim 7 having the name metallocene (cyclopentadienyl) (butanyl cyclopentadienyl) zirconium (IV) chloride.

9. A metallocene according to claim 7 having the name ((fluorenyl) (butanyl cyclopentadienyl) (dimethyl) methane) zirconium (IV) chloride.

10. A metallocene according to claim 7 having the name ((fluorenyl) (butanyl indenyl) dimethyl silane) zirconium (IV) chloride.

11. A metallocene according to claim 7 having formula (II) wherein the Z attached to R" is cyclopentadienyl, the other Z is fluorenyl, R is dimethylmethylene, R" is the saturated divalent ethylene radical, Me is Zr, and Q is Cl.

* * * * *

UNITED STATES PATENT AND TRADEMARK OFFICE
CERTIFICATE OF CORRECTION

PATENT NO. : 5,654,454

DATED : August 5, 1997

INVENTOR(S) : Bernd Peifer et al

It is certified that error appears in the above-identified patent and that said Letters Patent is hereby corrected as shown below:

Column 12, line 36, please delete "have" and insert therefor ---having---.

Signed and Sealed this

Twenty-first Day of October 1997

*Attest:*

BRUCE LEHMAN

*Attesting Officer*      *Commissioner of Patents and Trademarks*